United States Patent [19]

Kreft, III et al.

[11] Patent Number: 4,642,347

[45] Date of Patent: Feb. 10, 1987

[54] 3(2-QUINOLINYLALKOXY)PHENOLS

[75] Inventors: Anthony F. Kreft, III, Devon; Thomas W. Pattison, King of Prussia; John H. Musser, Malvern, all of Pa.

[73] Assignee: American Home Products Corporation, New York, N.Y.

[21] Appl. No.: 736,618

[22] Filed: May 21, 1985

[51] Int. Cl.⁴ ............................................ C07D 215/16
[52] U.S. Cl. .................................... 546/181; 544/349; 544/336; 548/165; 548/217; 548/305
[58] Field of Search ........................................ 546/181

Primary Examiner—Glennon H. Hollrah
Assistant Examiner—D. B. Springer
Attorney, Agent, or Firm—George Tarnowski

[57] ABSTRACT

There are disclosed compounds of the formula

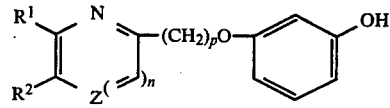

wherein Z is CR or N, when n=1; or Z is O, S, or NR, when n=0; n is 0 or 1; p is 1-10; $R^1$ is hydrogen, loweralkyl, loweralkoxy or halo; $R^2$ is hydrogen, loweralkyl, loweralkoxy or halo; or $R^1$ and $R^2$ taken together form a benzene ring; and the pharmaceutically acceptable salts thereof, and their use in the treatment of leukotriene-mediated naso-bronchial obstructive airpassageway conditions, such as allergic rhinitis, allergic bronchial asthma and the like.

2 Claims, No Drawings

3(2-QUINOLINYLALKOXY)PHENOLS

This invention relates to novel resorcinol monoether compounds possessing lipoxygenase inhibitory and slow-reacting substance of anaphylaxis (SRS-A) antagonist activity which are useful as antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of these AA metabolites has been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes $LTC_4$, $LTD_4$ and $LTE_4$ [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

The biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis and asthma must focus on either inhibiting synthesis of mediators of these conditions or antagonizing their effects. Thus, compounds which inhibit the biological effects of the leukotrienes and/or which control the biosynthesis of these substances, as by inhibiting lipoxygenase, are considered to be of value in treating such conditions as allergic bronchial asthma, allergic rhinitis, as well as in other immediate hypersensitivity reactions.

The invention provides novel compounds of the formula

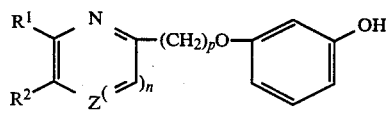

wherein
Z is CR or N, when n=1; or Z is O, S, or NR, when n=0;
n is 0 or 1;
p is 1–10;
$R^1$ is hydrogen, loweralkyl, loweralkoxy or halo;
$R^2$ is hydrogen, loweralkyl, loweralkoxy or halo; or
$R^1$ and $R^2$ taken together form a benzene ring;
and the pharmaceutically acceptable salts thereof.

The term "halo" refer to fluoro, chloro and bromo. The terms "loweralkoxy" and "loweralkyl" refer to moieties having 1–6 carbon atoms in the carbon chain.

The compounds of the invention can be prepared in the following manner:

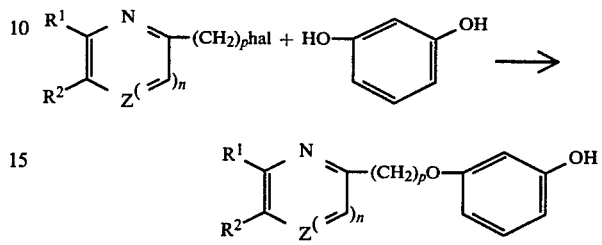

wherein Z, n, p, $R^1$ and $R^2$ are as defined hereinbefore and hal refers to a halo radical, for example, chloro or bromo. The reaction is carried out in an organic solvent, for instance, ethanol in the presence of a base under a nitrogen atmosphere.

The starting compounds in the above preparative sequence are commercially available or can be prepared by conventional methods known in the art.

The compounds of the invention are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic, oxalic and the like.

The compounds of the invention, by virtue of their ability to inhibit the activity of lipoxygenase enzyme and by their ability to antagonize the effect of $LTD_4$ and $LTC_4$, which are the major constituents of SRS-A, are useful for the inhibition of symptoms induced by these leukotrienes. Accordingly, the compounds are indicated in the prevention and treatment of those disese states in which $LTD_4$ and $LTC_4$ are causative factors, for example, allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders, they can be formulated into oral dosage forms such as tablets, capsules and the like. The componds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE and the cyclooxygenase product $PGE_2$; the ability of the compounds to antagonize $LTC_4$ and $LTD_4$-induced bronchospasm mediated by exogenously administered leukotrienes; demonstrate the in vivo activity of the compounds as lipoxygenase inhibitors and leukotriene antagonists of endogenous mediators of bronchospasm; and demonstrate the ability of the compounds to inhibit the synthesis of $TxB_2$.

The following examples show the preparation and pharmacological testing of compounds within the invention.

EXAMPLE 1

3-(2-Quinolinylmethoxyl)phenol

To a solution of 15.0 g (70.1 mm) of 2-chloromethylquinoline hydrochloride and 7.71 g (70.1 mm) of resorcinol in 50 ml ethanol under nitrogen is added over 30 minutes dropwise a solution of 9.1 g (140.0 mm) potassium hydroxide in 50 ml ethanol. After addition is complete the reaction mixture is refluxed for 2 hours. The solution is allowed to come to room temperature; the precipitate is then filtered off. The mother liquor is evaporated and the residue is triturated with methylene chloride. Evaporation of the organic solvent gives 10.0 g of crude product. HPLC purification affords 4.6 g of a white solid which when recrystallized from toluene affords white crystals, m.p. 153°–155° C.

Analysis for: $C_{16}H_{13}NO_2$ Calculated: C, 76.48; H, 5.21; N, 5.58 Found: C, 76.38; H, 5.31; N, 5.64.

EXAMPLE 2

The compounds of 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. This is especially true with respect to 5,12-diHETE, which is also denoted as $LTB_4$ [see Ford-Hitchinson, *J. Roy. Soc. Med.*, 74, 831 (1981)]. The assay of this Example measures the ability of the compounds of the invention to inhibit the synthesis of 5-HETE and $LTB_4$ by rat glycogen-elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 $\mu$M), A23187, is added together with 0.5 $\mu$Ci [$^{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system—hexane:ether:acetic acid (50:50:3). After chromatography, the areas associated with 5-HETE standard are identified by autoradiography, cut out and quantitated by liquid scintillation.

Results are expressed as % inhibition of [$^{14}$C]5-HETE synthesis.

$$\% \text{ inhibition} = \frac{\text{control} - \text{test}}{\text{control}} \times 100$$

The compound of Example 1 is tested in this assay, along with the closely related compound 2-(2-quinolinylmethoxy)phenol, which is disclosed to be an antiinflammatory agent in U.S. Pat. No. 4,244,956. The following results are obtained.

TABLE I

| Compound | 50% Inhibitory Concentration ($IC_{50}$) $\mu$M 5-HETE |
| --- | --- |
| Example 1 | 6.07 |
| 2-(2-quinolinylmethoxy)phenyl | 53.0 |

The results show that the compound of Example 1 is approximately an order of magnitude more potent than the prior art compound in inhibiting the synthesis of 5-HETE by rat peritoneal neutrophils. This indicates that the compound of Example 1, as opposed to the prior art compound, exhibits significant 5-lipoxygenase inhibition.

EXAMPLE 3

The procedure of Example 2 is also employed for the determination of the ability of the compounds of the invention to inhibit the synthesis of the arachidonic acid cyclooxygenase oxidation products $TxB_2$ and $PGE_2$.

In this assay, the procedure of Example 2 is carried out as described. However, in order to determine cyclooxygenase activity, the samples are cochromatographed with authentic reference $TxB_2$ and $PGE_2$ in the solvent system ethyl acetate:formic acid (80:1) and the upper phase of ethyl acetate:isoctane:acetic acid:water (110:50:20:100). After chromatography, the areas associated with TxB$_2$ and PGE$_2$ standards are identified by autoradiography, cut out and quantitated by liquid scintillation techniques.

The results are calculated as in Example 2 and presented below.

Testing compounds of this invention in this assay, the following results are obtained.

TABLE II

| Inhibition of Synthesis of TxB$_2$ | |
| --- | --- |
| Compound | % Inhibitory Concentration (IC$_{50}$) μM |
| Example 1 | 14.6 |
| 2-(2-quinolinylmethoxy)phenol | 6.82 |
| Inhibition of Synthesis of PGE$_2$ | |
| Compound | 50% Inhibitory Concentration (IC$_{50}$) μM |
| Example 1 | >100 |
| 2-(2-quinolinylmethoxy)phenol | 5.82 |

The results show that while both compounds inhibit the synthesis of the cyclooxygenase product, TxB$_2$, the prior art compound is twice as potent as the compound of Example 1 in this respect. Even more striking is the failure of the compound of Example 1 to influence the synthesis of PGE$_2$, while the prior art compound is quite significantly active in this regard.

These results taken with those reported in Example 2, support the conclusion that the compound of Example 1 is inversely related to the prior art compound as regards its effect on 5-lipoxygenase and cyclooxygenase reactions, i.e., the former is a strong inhibitor of 5-lipoxygenase, while having little or no significant cyclooxygenase inhibitory activity.

EXAMPLE 4

The assay of this Example measures the in vivo ability of the compounds of the invention to inhibit the bronchospasm induced in guinea pigs by the exogenously administered leukotrienes C$_4$ and/or D$_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for LTC$_4$ range from 1 to 2 μg/kg and for LTD$_4$ the range is from 0.3 to 1 μg/kg. The aerosol bronchoprovocation dose for LTC$_4$ is generated from 1.6 μM solution and for LTD$_4$ from a 2.0 μM solution.

Test drugs are administered either intravenously, by aerosol or orally at 1 or 10 minutes before induction of bronchospasm by administration of either LTC$_4$ or LTD$_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\% \text{ max } AUC = \frac{3(1 \text{ min}) + 4(3 \text{ min}) + 2(5 \text{ min})}{10(\text{max})} \times 100 \quad (1)$$

Drug effects are reported as percent inhibition of % max AUC values obtained from appropriate control animals (equation 2):

$$\% \text{ inhibition} = \quad (2)$$

$$\frac{\% \text{ max } AUC \text{ control} - \% \text{ max } AUC \text{ treated}}{\% \text{ max } AUC \text{ control}} \times 100$$

Student's t-test for unpaired data is used to determine statistical significance.

As in Examples 2 and 3, the compound of Example 1 and the prior art compound discussed in Example 2 are tested in this assay. The results for these compounds are as follows:

TABLE III

| | Compound administered intraduodenally at 10 minutes before induction of bronchospasm | | |
| --- | --- | --- | --- |
| Treatment | Dose mg/kg | % Maximal Bronchoconstriction | % Inhibition |
| Expt. 1 | | | |
| Control | — | 56 ± 6 | — |
| Compound of Example 1 | 50 | 10 ± 1 | 82*** |
| Expt. 2 | | | |
| Control | — | 60 ± 4 | — |
| 2-(2-quinolinylmethoxy)phenol | 50 | 43 ± 6 | 28* |

*P < 0.05;
***P < 0.001 compared to its control.

These results demonstrate that the compound of Example 1 is approximately three times more potent than the prior art compound as an inhibitor of LTD$_4$-induced bronchoconstriction. This is a significant profile for a compound useful in the treatment of allergic airways disorders.

EXAMPLE 5

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition } = \quad (2)$$

$$\frac{\% \max AUC \text{ control} - \% \max AUC \text{ treated}}{\% \max AUC \text{ control}} \times 100$$

Students t-test for unpaired data is used to determine statistical significance.

Following the test patterns of Examples 2–4, the compound of Example 1 and the prior art compound, 2-(2-quinolinylmethoxy)phenol are tested in the above-outlined assay with the following results:

TABLE IV

| Treatment | Dose mg/kg | % Maximal Bronchoconstriction | % Inhibition |
|---|---|---|---|
| Expt. 1 | | | |
| Control | — | 45 ± 9 | — |
| Compound of Example 1 | 50 | 21 ± 8 | 53* |
| Expt. 2 | | | |
| Control | — | 59 ± 2 | — |
| 2-(2-quinolinyl-methoxy)phenol | 50 | 31 ± 6 | 47*** |

*P < 0.05;
***P < 0.005 compared to its control.

The results show the compounds tested to be equipotent against ovalbumin-induced bronchoconstriction.

In summary, the data presented in the above-pharmacological examples demonstrates that the compound of Example 1 is a very potent 5-lipoxygenase inhibitor as well as a potent leukotriene antagonist. This profile makes it valuable in the treatment of allergic airways disorders, especially suitable in the treatment and prevention of allergic bronchial asthma. The prior art compound tested, by virtue of its potent activity as a cyclooxygenase inhibitor, with ability to block leukotriene responses, makes it valuable for precisely the indications claimed for it in U.S. Pat. No. 4,244,956, as an anti-inflammatory agent.

What is claimed is:

1. A compound having the formula:

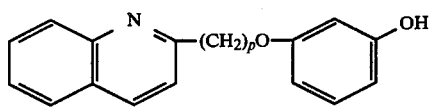

wherein p is 1–4, and the pharmaceutically acceptable salts thereof.

2. The compound of claim 1, which is 3-(2-quinolinylmethoxy)phenol.

* * * * *